US00PP16069P2

(12) United States Plant Patent
Olesen et al.

(10) Patent No.: US PP16,069 P2
(45) Date of Patent: Oct. 25, 2005

(54) ***CLEMATIS* PLANT NAMED 'EVIPO019'**

(50) Latin Name: *Clematis viticella*
Varietal Denomination: Evipo019

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 78 days.

(21) Appl. No.: 10/787,268

(22) Filed: Feb. 26, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. 'Evipo019' flowers readily as a young plant, has a compact growth habit, profuse, violet blue flowers, and continuous summer flowering. The variety successfully propagates from softwood cuttings and is suitable for cultivation in commercial glasshouses. This new and distinct variety has shown to be uniform and stable in the resulting generations from asexual propagation.

1 Drawing Sheet

Botanical classification: *Clematis* l. Genus—*Clematis*. Species—*viticella*.

Variety denomination: 'Evipo019'.

Commercial classification: Early, large flowering cultivar.

SUMMARY OF THE INVENTION

The present invention constitutes a new and distinct variety of *Clematis* which originated from a controlled crossing between the female parent, an unnamed, non-patented seedling, and the male parent, an unnamed, non-patented seedling.

The new *clematis* may be distinguished from its female seed parent by the following combination of characteristics:

1. While the seed parent has flowers which are Violet Group 91D, flowers of 'Evipo019' are Violet Group N88C.
2. While the seed parent has an average flower size of 160 mm, the same of 'Evipo019' is 90 to 120 mm.

The new *clematis* may be distinguished from its male pollen parent by the following combination of characteristics:

1. While the pollen parent has flowers which are Violet Group 89A, the same of 'Evipo019' are Violet Group N88C.
2. While the pollen parent has flowers which are 150 mm on average, the same of 'Evipo019' are smaller, measuring 90 to 120 mm.

The two parents were crossed and the resulting seed was planted in a controlled environment. The new variety is named 'Evipo019'.

The objective of the hybridization of this *Clematis* variety for commercial glasshouse and nursery culture was to create a new and distinct variety with unique qualities such as :

1. Light violet flowers;
2. Free and early flowering;
3. Exceptional compact growth habit;
4. Flowers well as a young plant;
5. Suitability for container culture.

These qualities required improvement in *Clematis* varieties that were in commercial cultivation and the objectives have been substantially achieved in the new variety, as evidenced by the unique combination of characteristics that are present in 'Evipo019' which distinguish it from all other varieties of which we are aware.

'Evipo019' was selected by Raymond J. Evison and Mogens N. Olesen in their *Clematis* development program in Domarie Vineries Les Sauvagees, St. Sampsons, Guernsey, Channel Islands, United Kingdom in April 1998. Asexual reproduction of 'Evipo019' by cuttings was first done by Raymond J. Evison and Mogens N. Olesen in Domarie Vineries Les Sauvagees, St. Sampsons, Guernsey, Channel Islands, United Kingdom in May 1998. This initial and subsequent propagations have demonstrated that the characteristics of 'Evipo019' are true to type and are transmitted from one generation to the next.

BRIEF DESCRIPTION OF THE DRAWING

The accompanying color illustration show as true as is reasonably possible to obtain in color photographs of this type:

FIG. 1.1 Bloom, upper side;
FIG. 1.2 Bloom, lower side;
FIG. 1.3 Flower buds at various stages of development;
FIG. 1.4 Juvenile stem, flower bud, and leaves;
FIG. 1.5 Mature compound leaf;
FIG. 1.6 New growth, including stem and juvenile leaves.

DETAILED DESCRIPTION OF THE VARIETY

The following is a detailed description of 'Evipo019', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Xeres', a non-patented variety. Chart 1 detailes a comparison of several physical characteristics of 'Evipo019' and the comparison variety.

CHART 1

| | 'Evipo019' | 'Xeres' |
|---|---|---|
| Typical growth in one season | Compact: Season's growth is 1 to 1.5 meter. | Average: Season's growth is greater than 2.0 meters. |
| Flowering characteristic | Flowers well as a young plant. | Does not flower well as a young plant. |
| Tepal Color (upper surface) | Violet Group N88C. | Violet Group N88B. |
| Flower diameter | 90 to 120 mm. | 150 to 180 mm. |
| Vegetative stem and petiole color | Green Group 137C. | Red-Purple Group 59A. |

FLOWER AND FLOWER BUD

Blooming habit: Recurrent. Flowering in May, June, August, and September.

Flower bud:

*Size.*—30 to 40 mm in length. 13 mm in diameter on average.

*Bud form.*—Ovoid.

*Bud color.*—Green Group 138C at ¼ opening.

*Tepals.*—Violet Group N88C upon opening.

Peduncle:

*Surface.*—Smooth.

*Length.*—60 to 90 mm.

*Diameter.*—1 to 2 mm.

*Color.*—Green Group 137C.

*Strength.*—Moderately strong. Flowers maintain an upright attitude on plant.

Receptacle: None observed.

Flower arrangement:

*Location on vine.*—New and old growth.

*Borne.*—In clusters resembling compound cymes.

Flower bloom:

*Size.*—90 to 120 mm in diameter. Flower depth is 25 mm on average.

*Profile.*—Upon opening, flowers are flat to concave with straight tepals.

*Color.*—Upon opening: Upper surface is Violet Group N88B. The reverse side is Violet Group N88D at the margins, with a central bar at the mid rib of the tepal, which is Green Group 137D in color. After opening: Upper surface is Violet Group N88C. The reverse side is Violet Group N88D with a central bar at the mid rib of the tepal, which is Green-White Group 157A in color.

*Fragrance.*—Very light, floral scent.

*Lasting quality.*—On the plant, flowers persist from 10 to 20 days. As a cut flower, short in duration, from 1 to 4 days.

Tepals:

*Quantity.*—8 tepals on average. Occasionally, flowers develop 2 to 4 inner tepals shorter in length.

*Shape.*—Elliptic. Base shape is acute.

*Size.*—45 mm in length, on average. 25 mm wide, on average.

*Cross section.*—Flat.

*Margins.*—Entire. Weak undulations.

*Tepal apex.*—Acute.

*Apex recurvature.*—Occasional.

*Persistence.*—Tepals drop off cleanly from the plant after flowers have matured completely.

*Arrangement.*—Regular.

Reproductive organs:

*Arrangement.*—Compact.

*Pollen color.*—Yellow Group 2D.

*Anthers.*—Color: Purple Group N79A.

*Filaments.*—Color: White Group 155C. Length: 8 mm.

*Pistils.*—Length: 9 mm. Quantity: Normally 60 to 70 per flower.

*Stigmas.*—Slightly superior relative to the length of the filaments and the height of the anthers.

PLANT

Plant form: Climbing and spreading.

Plant growth: Compact.

Size: Seasons growth attains 1 to 1.5 meters in height.

Hardiness: Trials to date show the variety is cold tolerant to USDA cold hardiness zone 4.

Stems:

*Color.*—Young wood: Green Group 137C. Older wood: Greyed-Red Group 178B.

*Internodes.*—Shape: Cylindrical. Length: 80 to 150 mm.

*Surface.*—Young wood: Smooth. Older wood: Smooth.

*Length.*—Normally 0.75 to 1.5 meters.

*Diameter.*—2 to 3 mm.

Plant foliage:

*Leaf characteristics.*—Deciduous.

*Mature leaf form.*—Pinnate. There are 3 leaflets.

*Compound leaf size.*—150 mm (l)×180 mm (w).

*Color.*—Upper surfaces of mature leaves are Green Group 137A in color. Lower leaf surface is Green Group 137B. Upper surfaces of new foliage are Green Group 137C. Lower surfaces are Green Group 137C.

Plant leaves and leaflets:

*Stipules.*—Absent.

*Petioles.*—Size: 60 to 90 mm in length. Color: Green Group 137C. Clasping: Winding leaf petiolus.

*Petioloule.*—Length: 15 to 50 mm. Color: Green Group 137C.

*Leaflet shape.*—General shape: Ovate. Occasionally cordate. Base: Rounded. Apex: Acute.

*Margin.*—Entire.

*Leaflet size.*—60 mm in length by 30 mm wide.

*Texture.*—Smooth.

*Surface.*—Upper side: Glabrous. Lower side: Ribbed.

*Thickness.*—Medium thickness.

*Glossiness.*—Matte.

Disease resistance: Subject to any disease that normally attacks the species.

What is claimed:

1. A new and distinct variety of *clematis* plant named 'Evipo019' as illustrated and described herein, due to its abundant light violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

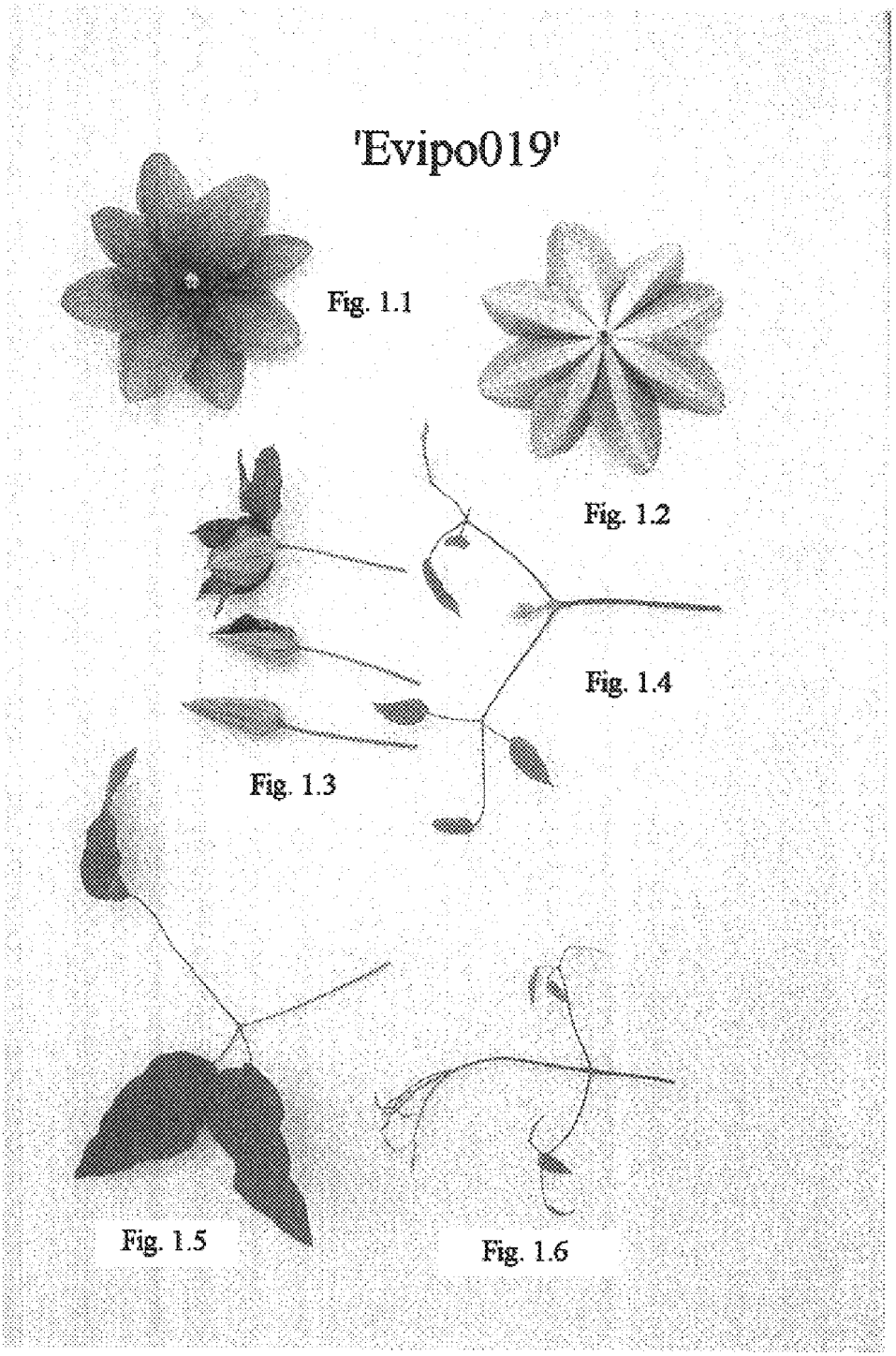
'Evipo019'
Fig. 1.1
Fig. 1.2
Fig. 1.4
Fig. 1.3
Fig. 1.5
Fig. 1.6